United States Patent [19]

Dirheimer et al.

[11] 4,213,970

[45] Jul. 22, 1980

[54] ANTIVIRAL COMPOSITIONS CONTAINING A TRANSFER-RIBONUCLEIC ACID

[75] Inventors: Guy Dirheimer, Strasbourg; Pierre Louisot, Lyons, both of France

[73] Assignee: Boehringer Ingelheim GmbH, Ingelheim am Rhein, Fed. Rep. of Germany

[21] Appl. No.: 48,671

[22] Filed: Jun. 14, 1979

[30] Foreign Application Priority Data

Jun. 3, 1978 [DE] Fed. Rep. of Germany ....... 2824411

[51] Int. Cl.² .................. A61K 31/70; A61K 31/665; C07H 21/02

[52] U.S. Cl. .................................... 424/180; 536/28; 536/29

[58] Field of Search .................... 536/28, 29; 424/181, 424/180

[56] References Cited

U.S. PATENT DOCUMENTS

| | | |
|---|---|---|
| 3,821,193 | 6/1974 | Fare et al. ............................... 536/28 |
| 3,966,707 | 6/1976 | Chain et al. ............................ 536/28 |
| 4,124,702 | 11/1978 | Lampson et al. ...................... 536/28 |

OTHER PUBLICATIONS

England et al., "Canadian Jour. Chem.," vol. 54, No. 11, pp. 1714–1721, 6/76.

*Primary Examiner*—Johnnie R. Brown
*Attorney, Agent, or Firm*—Hammond & Littell, Weissenberger & Muserlian

[57] ABSTRACT

Antiviral pharmaceutical compositions containing as the active ingredient a eukaryotic transfer-ribonucleic acid, and a method of treating viral infections therewith.

4 Claims, No Drawings

ANTIVIRAL COMPOSITIONS CONTAINING A TRANSFER-RIBONUCLEIC ACID

This invention relates to novel antiviral pharmaceutical compositions containing as the active ingredient a eukaryotic transfer-ribonucleic acid (t-RNA), as well as to a method of treating viral infections therewith.

BACKGROUND OF THE INVENTION

It is known that in cells of vertebrate animals protection against damage by virus infections can be obtained by means of a contact between viruses and certain other microbial substances. It is assumed that this contact induces the formation of materials which hinder the viruses that have penetrated the cell in their replication. The biochemical mechanism of the antiviral activity is still under discussion. The induced antiviral proteins—for example, the interferon—are specific to virus species.

Therefore, it is of great significance to find suitable inducers which cause directly in the human organism the formation of these inhibiting proteins, which are then at the disposal for general defense against viruses.

A survey of the activity of substances tested for their interferon-inducing action according to prior art is given in Table I (R. F. Beers and W. Braun "Biological Effects of Polynucleotides"; published by Springer Verlag Stuttgart, Germany, 1971).

Table I

| Polynucleotide | i.v. dose per rabbit (µg) | Interferon-titre (rabbit) |
| --- | --- | --- |
| Poly I:C | 2 | 640 |
| Poly A:U | 25 | 20 |
| RNA from Reovirus 3 | 8 | 640 |
| RNA from M S 2 Coliphagen | 8 | 160 |
| RNA from M U 9 Coliphagen-Mutants | 2 | 40 |
| RNA from *Escherichia coli* | 100 | 0 |
| RNA from Influenza virus | 10 | 0 |
| Total RNA yeast | 100 | 0 |
| t-RNA from yeast | 200 | 0 |
| RNA from yeast ribosomes | 1000 | 0 |
| t-RNA from bovine liver | 200 | 0 |

As the table by way of the example for the interferon titre shows, the intensity of the inducing activity differs greatly; the partially synthetically obtained Poly I:C is very effective, for example, while the transfer-ribonucleinic acids (t-RNA) do not show any effect here.

As a measure of the activity of an inducing substance, the antiviral effectiveness is employed. It is determined in vitro as the inhibition of the infective activity of a virus in a cell culture, where the number of the plaques that are formed in the cell-lysis caused by infection is determined. [Finter, N. V.: Interferon Assays and Standards; in "Interferons" (North-Holland Publ. Company, Amsterdam, Holland, 1966).—Lorenz, R. J.: Zur Statistik des Plaque—Testes, Arch. Ges. Virusforsch. 12, 108–137 (1963)].

In the in vivo test a number of animals are infected by a virus in a specific range of the lethal dose, and the increase of the rate of surviving animals or the decrease of the symptoms of the disease or the number of the virus genes in the blood (viremia) is determined by means of the inducing substance.

Due to its high effectiveness, Poly I:C was generally found to be of theoretical and practical interest. For example, it has been used against local keratitis in the eye; but a systemic use in human organisms is prevented by its toxicity, which is comparable to that of endotoxin [see M. Absher and W. Stineberg, Nature 223, page 715 (1969), as well as H. L. Lindsay, P. W. Trown and J. Brandt, Nature 223, page 717 (1969)].

DESCRIPTION OF THE INVENTION

During our search for other, non-toxic, effective inducers, we have discovered that the eukaryotic t-RNA made from yeast, for example, which has been considered to be ineffective according to prior art [see Table I above, as well as the work of Stebbing et al (J. gen.Virol. (1977), 34, page 73–83)] possesses in vitro as well as in vivo a good antiviral activity. The latter does not always run parallel to a corresponding interferon titre by any means, so that concurrently other inhibiting principles must be postulated. This may also be the reason why this antiviral activity—indirectly measured by way of an interferon titre—has not heretofore been described for eukaryotic t-RNA. Moreover, a high purity of the t-RNA plays an important part in its antiviral activity. In a test on mice, no toxicity of this t-RNA could be detected even at a concentration several thousand times the effective range.

A suitable starting material for obtaining active t-RNA is, besides the yeast preferably used (especially various brewer's and baker's yeasts), also fungus mycelium (for example, of Aspergillus niger) as well as the liver of mammals.

The compositions of this invention may be used for the treatment of all non-carcinogenic diseases caused by viruses, such as colds, influenza, measles, German measles, herpes, encephalitides and polyomyelitis. They may be used in human as well as veterinary medicine. The single effective dose is from 1 to 150 mgm, preferably 10 to 15 mgm, depending upon the patient to be treated or the virus to be controlled. The administration is preferably effected directly on the infected oral or nasal membranes, preferably by means of, for example, aqueous sprays or in the form of a solution or ointment (topical administration), but administration by injection is also possible. It is also possible to add adjuvants to t-RNA, such as methylated albumin, protamine sulfate, neomycin, streptomycin, lysozym, DEAE-dextran or arginine, in order to intensify the effect. The dosage units of these adjuvants are about 100 times higher than those of the t-RNA.

EXPERIMENTAL PART

A. Production of t-RNA from yeast

EXAMPLE 1: Preparation from brewer's yeast of the brewery Kronenbourg, Strasbourg, France.

The crude t-RNA was obtained in analogy to the method described by R. S. Holley in *Methods in Enzymology*, Vol. XII, page 596.

11 kg of yeast are suspended in 11 liters of 88% phenol and 25 liters of distilled water (stirring with glass rod and stirring motor). The mixture is allowed to stand until the phases have separated. Normally, this will be reached after 7 to 10 days. The upper aqueous phase is siphoned off and mixed again with 1 liter of 88% phenol and allowed to stand overnight. Then, the clear yellow supernatant is siphoned off (aqueous phase) and admixed with 150 ml of a 20% potassium acetate solution of pH 5.2, subsequently it is precipitated with 32 liters of 96% ethanol. After 24 hours the clear supernatant is sucked off and discarded. The suspension containing the precipitate is centrifuged and washed with a little ethanol. The yellowish-brown precipitate is dissolved afterwards in 0.1 M tris-buffer of pH 7.5. The clear supernatant is siphoned off and collected. In the meantime, 190 gm of DEAE-cellulose (normal) were treated with 1 liter of 0.1 M NAOH (not longer than 20 minutes), washed with distilled water (freshly double-distilled) and treated subsequently with 1 liter of 0.1 M HCl. Thereafter, the DEAE-cellulose is washed with distilled water and with 4 liters of buffer tris-HCl 0.1 M, pH 7.5. The cellulose thus prepared is filled into a glass column ($8 \times 40$ cm). On this column is given the above RNA solution (2.3 liters), whereby the ribonucleic acids are adsorbed. The eluate is discarded, and the column is washed with 20 liters of 0.1 M tris buffer of pH 7.5.

This eluate is also discarded. Subsequently, the nucleinic acids are eluted with 5 liters of 0.1 M tris buffer of pH 7.5 which is 1 M in NaCl. The eluate is admixed with 10 liters of 96% ethanol and allowed to stand overnight. The next morning the supernatant is siphoned off and discarded, the precipitation is centrifuged and washed with 500 ml of 80% ethanol and subsequently with 500 ml of 96% ethanol. The yield of t-RNA after freeze-drying is about 12 gm.

Care should be taken that all these operations are carried out under sterile conditions.

According to the above method, a t-RNA-preparation was also prepared from baker's yeast of the Société Industrielle de Levure "Fala" (rue St. Nazaire, Strasbourg, France).

B. Characterization of the t-RNA-fraction (from Kronenbourg brewer's yeast) by means of physico-chemical methods (1) Column-chromatographic behavior:
   Chromatography on Sephadex G 100 (see Determann, Gelchromatographie, Springerverlag 1967, page 72) yielded Kd-values of 0.35–0.37.
(2) UV-Absorption:
   The value for the ratio of the absorption degree at the absorption maximum (258 nm) and at the absorption minimum (280 nm)

$A_{258}/A_{280}$ is 2.09 (literature: about 2.0)
(3) Gel electrophoresis:
   The gel electrophoresis was performed according to J. Gangloff, G. Keith, J. P. Ebel and G. Dirheimer, Biochim. Biophyl. Acta 259, 210–222, at page 212 (1972) in polyamide gel (12%, 7 molar urea, pH 8.1). Measurement of the ions took place without coloring in the UV.
(4) Hyperchromicity
   The hyperchromicity, that is, the increase of the degree of absorption due to the dissolution of hydrogen bonds in the polynucleotide double helix upon an increase of temperature, was determined in accordance with *Methods in Enzymology*, Vol. XII, part B, (1968, L. Grossman, K. Moldave, Academic Press) page 247. As solvent served 0.01 M cacodylate buffer (pH 7), which was 0.01 M in MgCl$_2$. The increase of the degree of absorption at 260 nm was 31% when heating to 100° C.
(5) Melting point
   The "melting point" as turning point of the S-shaped curve for the function absorption degree (260 nm)/temperature (see *Methods in Enzymology*, Vol. XII, part B, 1968, L. Grossman, K. Moldave, Academic Press, page 194) resulted in a mean value of 71° C.

As solvent served again 0.01 M cacodylate buffer (pH 7), which was 0.01 M in MgCl$_2$.
(6) Total hydrolysis (base composition)
   The total hydrolysis and the determination of the nucleosides were performed according to J. Gangloff, G. Keith, J. P. Ebel and G. Dirheimer, Biochim. Biophys. Acta 259, 198–209, namely at page 201 (1972). The following values were obtained:
   A$^{(x)}$—21%
   U—16.5%
   G—31%
   C—26%
   Ψ—4%
   T—1.7%

$^{(x)}$Abbreviations acc. to Eur. J. Biochem. 15, 203 (1970)
(7) Charging with amino acids
   The method is described by G. Dirheimer and J. P. Ebel, Bull. Soc. Chim. Biol. 49, 1679–1687, namely at page 1681 (1967). As amino acids were used [$^{14}$C]-alanine and [$^{14}$C]-valine. The charging yielded for
   alanine: 4%
   valine: 14%

C. Determination of the anti-viral activity

For some of the tests described below, poly I:C (Miles) was used as a comparative preparation.

(1) Inhibition of a Sindbis virus infection in the mouse 2 and 10 μgm, respectively, of the test substance in 0.2 ml of buffer were administered i.v. to groups of 5 mice each (OF-1/IFFA'CREDO). As comparative substance serves the well-tested, but partly toxic, synthetic polynucleotide poly I:C. The control consists of an i.v. administration of 0.2 ml of buffer solution. 24 hours later, a defined quantity of Sindbis virus (RNA-virus of the Arbo group) in 0.25 ml of PBS-buffer is administered intraperitoneally to the mice. After another 24 hours the mice are decapitated, the pooled serum is diluted stepwise and tested in the tissue culture (chicken fibroblast) for still present viruses.

Thus, by pre-treatment with 2 μgm test substance, the viremia titre may be decreased, for example, from 1:100,000 (virus control without t-RNA administration) to 1:80 (the comparative substance poly I:C lies in the same order of magnitude. Analogous results could be reproduced in numerous experiments. It is of interest that also the pure t-RNA$_1^{THR}$ at 10 μgm/mouse can reduce the virus titre from 1:5000 to 1:200. A defined fraction of 22 polynucleotide particles of same also shows an effect with a decrease of the viremia from 1/5000 to 1/500.

METHODS

Virus:

Young mice in the age of 2 to 6 days are administered intracerebrally a drop of a Sindbis virus suspension AR 339 with the titre 10$^5$PFU/ml. After 42 hours the brains of the surviving animals are taken out, the organ material is triturated sterile at 4° C. in a salt solution according to J. H. Hanks and R. F. Wallace, Proc. Soc. Exptl. Biol. Med. 71 196–200 (1949) (5 ml of solution for the brains of 4 mice), and the obtained suspension is kept in sealed ampules at 4° C.

Cell culture

A suspension of $10^6$ chicken embryo fibroblasts per ml of a salt solution according to J. H. Hanks and R. E. Wallace, Proc. Soc. Explt. Biol. Med. 71, 196–200 (1949) is prepared, to which 0.5% lactalbumin hydrolysate, 0.1% of yeast extract, 10% of calf serum, 200 units of penicillin and 50 mg of streptomycin are added. 5 ml each of this suspension are given into Petri dishes of 7 cm diameter, and these are kept in sealed containers in a 10% $CO_2$ atmosphere at 37° C. in a heating cabinet. After 48 hours, an unbroken monocellular layer is obtained in the dishes.

(2) In vitro test with vesicular stomatitus virus (VSV)—infected fibroblasts; measurement of inhibition of plaques-formation by the serum of mice treated with an inducing substance.

In a further test arrangement the test substance is administered i.v. to the mice. After 24 hours the serum is obtained, and its anti-viral action is determined in the system fibroblast cell culture/VSV by the serial dilution method. This is a classic test arrangement for the proof of interferon formation. The greater the titre, the more effective the substance is. 2 μgm of t-RNA yield titres of about 1.160, 50 μgm of about 1:2560.

METHODS

Mice

Mice, one month old, of the strain $OF_1$, IFFA-CREDO (France), free from pathogenic microorganisms. The test substances are injected into the vein of the tail in a volume of 0.2 ml salt solution acc. to R. Earle (J. Natl. Cancer Instit. 4/page 165–212 (1943). After 24 hours the animals are killed, and their blood is removed; for the interferon titration, the serum is used.

Titration of the interferon 4 ml of a suitable dilution (referred to the potential interferon content) of the obtained mice serum are added to the cell culture, and it is incubated in a $CO_2$-atmosphere for 16 to 18 hours. Then, a dilution of the virus culture is added which yields a conveniently legible number of plaques (50–100), it is kept for another 48 hours in $CO_2$ at 37° C., and the plaques are counted after coloring with neutral red. The interferon titre is indicated as the dilution of the serum, which produces a decrease in number of plaques by 50%.

(3) In vivo test for anti-viral activity of t-RNA in the mouse against herpes-virus Lennette P 381

To each mouse 100 μgm t-RNA in 0.2 ml of buffer are administered i.v. For the controls only 0.2 ml of PBS are injected. 18 hours afterwards all animals receive $1-2 \times 10^6$ herpes viruses Lennette P 381 i.p.. At this time all mice are healthy.

| Day 0 | Animals without paralysis/ total number |
|---|---|
| Control | 26/26 |
| t-RNA | 27/27 |
| 12 days later the following condition had developed: | |
| Day 12 | Animals without paralysis/ total number |
| Control | 7/26 (27%) |
| t-RNA | 13/27 (48%) |

According to these results t-RNA exhibits a protective effect with respect to paralytic viral diseases.

METHODS

Mice

NMRI-mice, 3–4 weeks old

Virus

Herpes-virus Lennette P 381 (mouse-adapted, leads to characteristic paralysis of the extremities).

D. Toxicity

MIce, 2 months old, of the strain $OF_1$, IFFA-CREDO (France received quantities of t-RNA between 20 and 100 μgm under the same conditions as in the vivo-activity test. The subsequent infection with a virus preparation was omitted. In two series of tests all animals survived. Furthermore, in the serum as well as in the plasma the following determinations were made with the aid of the Technicon 10/60 autoanalyzer: $Ca^{++}$, phosphate, glucose, urea, uric acid, cholesterol, protein, albumin, bilirubin, kreatin, alk. phosphatase, lactic acid dehydrogenase.

No deviations from the standard resulted. I.v. administration of 0.5 mgm/kg in the dog produced after a single or six-day administration only a temporary increase of the transaminases and a decrease of the leucocytes. The serum electrophoresis shows no modifications in the protein fractions, as do the measurements of the remaining hematology, body temperature, body weight and consumption of food.

E. Examples for the use of the t-RNA-preparation in humans:

(1) Oral-nasal preparation

An effective composition for the prophylaxis against bronchially attacking viruses may be produced as follows:

0.2 gm of t-RNA isolated in accordance with the process described above are dissolved before use in 20 ml of sterilized distilled water (dry ampule) or in the conventional nose-drop liquid (distilled water containing a small quantity of reducing agent and complex-former). A dose of 20–50 mgm (i.e. approx. 1 to 5 ml) thereof is applied every 2 to 3 days by means of a pipette or a conventional atomizer to the endangered membranes (for example, the mucous membrane of the nose). 0.15 M phosphate buffer of pH 7.2 may also be used as the carrier liquid.

Furthermore, it is possible to suspend the t-RNA and to spray it directly upon the endangered membranes by metered aerosol. Dending upon the physician's instructions, this preparation may also be used every second to third day.

(2) Injection preparation

For production of such a preparation the t-RNA is suspended or dissolved in a conventional carrier, such as sesame oil. Advantageously, the concentration amounts to 10 to 50 mg per ml. The dosage unit packaging is effected in the usual way, by filling into sterile glass ampules and subsequent sealing.

(3) Injection preparation for i.v. administration

The lyophilized t-RNA filled into dry ampules is dissolved before use in a physiological common salt solution and then injected. Concentration as in 2.).

(4) Eye Preparation

In order to avoid as far as possible an irritation of the conjunctiva, it is best to use here an oily suspension, for example in peanut oil. The action ingredient concentration should be high enough to apply the required dose, i.e. about 20 to 50 mgm by means of 1 to 2 drops to the eye.

(5) Skin Preparation

For the treatment of lesions on the skin, t-RNA may be incorporated into conventional bases for ointments or lotions, where the active ingredient concentration is advantageously 1 to 150 mgm per 1 gm of base. It is to be used regularly every day or every other day according to the attending physician's instructions.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An antiviral pharmaceutical dosage unit composition consisting essentially of an inert pharmaceutical carrier and an effective antiviral amount of eukaryotic transfer-ribonucleic acid.

2. A composition of claim 1, where said transfer-ribonucleic acid is derived from yeast.

3. A composition of claim 2, where said transfer-ribonucleic acid is derived from brewer's yeast.

4. The method of treating non-carcinogenic viral infections in a warm-blooded animal in need thereof, which comprises parenterally or topically administering to said animal an effective antiviral amount of a composition of claim 1.

* * * * *